United States Patent
Klyukin

(10) Patent No.: US 7,214,194 B2
(45) Date of Patent: May 8, 2007

(54) METHOD FOR THERMAL DIAGNOSIS OF PATHOLOGY OF A BIOOBJECT AND DEVICE FOR CARRYING OUT SAID METHOD

(76) Inventor: Lemārk Mikhailovich Klyukin, Russia, 129336, Moscow, ul.Startovaya, d.21 ykv.69 (RU)

( * ) Notice: Subject to any disclaimer, the term of this patent is extended or adjusted under 35 U.S.C. 154(b) by 479 days.

(21) Appl. No.: 10/471,489

(22) PCT Filed: Jan. 8, 2002

(86) PCT No.: PCT/RU02/00002

§ 371 (c)(1), (2), (4) Date: Sep. 11, 2003

(87) PCT Pub. No.: WO02/071934

PCT Pub. Date: Sep. 19, 2002

(65) Prior Publication Data
US 2004/0097825 A1 May 20, 2004

(30) Foreign Application Priority Data

| Mar. 11, 2001 | (RU) | 2001106189 |
| Apr. 11, 2001 | (RU) | 2001109547 |
| Dec. 27, 2001 | (RU) | 2001135462 |

(51) Int. Cl.
*A61B 5/00* (2006.01)

(52) U.S. Cl. ..................................................... 600/549

(58) Field of Classification Search ................ 600/549, 600/474; 374/111, 112, 128, 107
See application file for complete search history.

(56) References Cited

U.S. PATENT DOCUMENTS

| 4,310,003 A | 1/1982 | Schlager | |
| 5,015,102 A * | 5/1991 | Yamaguchi | 374/107 |
| 5,820,263 A * | 10/1998 | Ciobanu | 374/111 |
| 6,440,084 B1 * | 8/2002 | Gentempo et al. | 600/549 |

FOREIGN PATENT DOCUMENTS

| RU | 2139671 | 10/1999 |
| RU | 2145483 | 2/2000 |

OTHER PUBLICATIONS

V.L. Dragun et al, Vychislitelnaya termo-grafiya. Primenenie v meditsine. Minsk, "Navuka I tekhnika", 1992, pp. 105-109.
V.V. Zaretzkiy et al, Clinical Thermography, Moscow, Medicine Publishing House, 1976, 3 p, 168 p.
G.I. Zenovko, Thermography in Surgery, Moscow, Medicine Publishing House, 1998, 10 p, 167 p).

* cited by examiner

*Primary Examiner*—Charles A. Marmor, II
*Assistant Examiner*—Fangemonique Smith
(74) *Attorney, Agent, or Firm*—Ladas & Parry LLP

(57) ABSTRACT

The invention relates to the field of medical equipment and is designed for the temperature diagnostics of bioobject pathologies. The method comprises dynamical measuring a body temperature in a series of points. Based on the difference temperature field on the surface of a body, zones are determined inside the bioobject that are identified with pathology loci. A temperature is each point is estimated with taking into account a type of skin of the bioobject, a type of a temperature sensor and the form of the sensor temperature change curve in process of measurement. The device comprises temperature measurement units, temperature sensors being connected to said temperature measurement units, a RAM unit, a program realization unit, a comparator unit, a programming unit, and a visualization unit. The invention allows to increase speed and reliability of exposing pathology loci.

8 Claims, 1 Drawing Sheet

METHOD FOR THERMAL DIAGNOSIS OF PATHOLOGY OF A BIOOBJECT AND DEVICE FOR CARRYING OUT SAID METHOD

FIELD OF THE INVENTION

The invention relates to biology and medicine. It can be used to estimate the internal state of a bioobject by detecting pathology loci in its body, in particular, for screening with the purpose of detecting and monitoring said loci in a human body.

BACKGROUND OF THE INVENTION

There is known a method for the temperature diagnostics of a human internal state by thermography, when the human internal state is judged by observing a temperature of a human skin at a distance from the body using a thermal imager (Zaretzkiy V. V., Vyhovskaya A. G., Clinical Thermography, Moscow, Medicine Publishing House, 1976, 3 p, 168 p.; Zenovko G. I., Thermography in Surgery, Moscow, Medicine Publishing House, 1998, 10 p, 167 p.). A distinctive feature of this method is that a skin surface temperature is judged from television observation results which depend not only upon the human skin surface temperature, but also upon its state which determines its radiating capability, upon a tilting angle of an observed surface zone relative to a lens axis of a thermal imager camera, and upon the conditions of skin radiation propagation through the atmosphere, which makes it difficult to estimate the skin surface temperature with the precision required for observing the influence of a pathology locus on the skin temperature, said pathology locus being hidden under a given surface area and having temperature different from the temperature of the same zone at a healthy body state.

Also known is a method for diagnosing the clinical state of a patient, comprising: consecutive basic measuring a temperature in a series of points of the patient's body when the patient is certainly well; comparing the temperature measured repeatedly in the same points and in the same order but some time later; calculating matrices of isotherms of said temperature values on the basis of differences; finding poles of said isotherms; and estimating a depth of a pathology locus using the resulting depth data (Method And Device For Diagnostics Of Patient Clinical Condition (L. M. Klukin), RU 2145483 C1 of Feb. 20, 2000). According to this method, a skin temperature of a patient is measured by a contact dynamic measurement mode along a grid of points covering all or a part of the patient's body. The dynamic mode of temperature measurement used in this method is based on the presumption that a value of a derivative of a curve reflecting a sensor temperature change with time, taken at its point directly after touching a surface to be studied, is inversely proportional to an asymptotic value it would have reached if a contact duration had been much longer than a sensor time constant. Since the derivative cannot be taken in principle at the very beginning of this curve, and also because it is difficult to select an exact value of a proportionality constant in the expression which links the derivative value with the asymptotic temperature value in each separate measurement, the asymptotic temperature value found using this method has quite considerable error which can exceed a temperature gradient taking place on a surface of the body of the bioobject and being caused by a pathology locus under said surface; as a result, this pathology locus will not be exposed.

Use of one sensor for diagnosing to solve the problem of examining a bioobject, as assumed in the known method, may take longer time than permissive because a proper temperature relaxation time of the body of the bioobject is less.

SUMMARY OF THE INVENTION

The purpose of the invention is to solve the problem of increase in the speed and reliability of exposing pathology loci; to this end, a value of an error taking place in measurement of a bioobject surface temperature at the dynamical measurement mode is decreased. The posed problem of decrease in a value of the measurement temperature error is accomplished by: previously establishing a form of a curve that expresses a temperature dependency of a sensor upon a time of measuring a temperature of a body skin surface after said sensor touches said surface; taking a great number of measurements at the beginning of the curve, whose number $n_3$ is chosen out of the condition of achieving a pre-set temperature error value which is $\epsilon = T_{2i} - T_{1i}$, where $T_{2i}$ is an asymptotic value of a predetermined temperature curve of heating the sensor at its contact with the skin of the bioobject, the temperature of each sensor before each measurement being set constant and equal to $T_{0i}$ which is kept at the required accuracy and is chosen out of the condition. $T_c \leq T_{0i} \leq T_{ki}$, where $T_{ki}$ is the lowest temperature of the skin of the bioobject in i-th point of measurements before their start, and $T_c$ is the temperature of the environment at the moment of measurements. To shorten a diagnosis procedure duration, the skin surface of the bioobject is marked with regular points, for instance, using applied masks with holes whose quantity is $n_1$ and the distances between them are chosen depending upon a size of the bioobject and a configuration of a body part to be studied, and examination in said points is carried out by temperature sensors whose quantity $n_2$ is chosen out of the condition of an optimal diagnosis duration.

To reveal a depth z of occurrence of a pathology locus and its nature, the magnitude values and sign of the temperature change in the zones are used where changes took place relative to an average temperature value $T_{cp}$ which is determined by results of the surface temperature measurement, while temperature changes as such in pathology loci may be represented by different colors whose intensity is set proportional to a value of said temperature change. If the temperature inside a pathology locus is higher than that of the surrounding tissue (inflammation, malignant tumor growth and others connected with increase of local metabolism), then, because an additional heat source presents, mapping of said temperature at a respective surface area of the body of the bioobject is accompanied by increase in the temperature whose gradient drops when a distance from a pole of corresponding isotherms increases. In this case, a depth z of occurrence of a pathology locus can be estimated, for instance, by the criterion:

$$Z \propto r \sqrt{\frac{2T^2}{T_0^2 - T^2} - 1},$$

where r is a current radius counted from an isotherm pole, $T_0$ is a temperature value at the isotherm pole, T is a current temperature value in polar coordinates with a center in the isotherm pole.

If the blood supply in a pathology locus is deteriorated (hematoma, non-malignant tumor, exudate, gangrene), such a locus may be considered as an area where normal heat evolution is absent, and a lower temperature is respectively observed in a pole of the isotherms within a bioobject surface area under which a respective pathology locus presents, and a depth z of occurrence of a pathology locus can be estimated, for instance, by the criterion:

$$Z \propto \sqrt{\frac{r^2}{\left(\frac{T_0}{T}\right)^{\frac{2}{3}}} - 1}$$

For the most dangerous pathology locus whose temperature is higher than an average temperature $T_{cp}$, an averaged temperature value in the pathology locus can be estimated, for instance, by the criterion:

$$T_{loc} \propto \frac{\Theta}{4\pi\rho} + T_{cp},$$

where $\Theta$ is a thermal current flowing on the surface and caused by the pathology locus with the higher temperature, $\rho$ is a typical pathology locus size which is calculated by information about z and a size of the pathology locus mapping on the surface.

Since coordinates of a center of isotherm poles and depths of occurrence of pathology loci fully determine the location of loci in corresponding organs of the body of the bioobject, and their size and the nature of temperature change in them are determined with such a determination, the pathology loci can be juxtaposed with nosology types known from thermographic observations, and it is possible to get a "typical" picture for each of observed nosology types based on statistically meaningful examinations of a sufficient number of identical bioobjects at similar diagnostic conditions. In that case, the "typical" picture data that are found can be used as spatial filters in analysis of results of current checkup, that is, the results of said checkup are considered as secondary in diagnostics of the body of the bioobject, and the "typical" pictures received before are to subtracted from said data.

The disclosed method allows to research the efficiency of action of various medical and biological factors and procedures to a pathology locus, said procedures being prescribed in order to eliminate said loci. By taking periodical pilot observations for pre-set time periods, it is possible to estimate the prescribed actions and recommend their further use or repeal if the result is positive.

In cases when there is no staff with sufficient qualification at the diagnosis site, e.g. when it is required to convene a medical consultation to estimate the diagnosis results, or if an urgent surgical operation is necessary, the diagnosis results can be sent by wireless communication as a file to a Medical Center specializing in treatment of corresponding types of nosologies.

To implement this method, a device is provided which comprises: a temperature measurement unit and a communication channel connected thereto, a RAM unit, a program realization unit as well as a comparator unit, a programming unit and a visualization unit all connected to the above-mentioned units by communication channels. To reduce a diagnosis time, a number $n_3$ of temperature measurement units can be chosen out of the inequality: $1 \leq n_3 \leq N$, where N is a number of organs of the bioobject to be tested, and said temperature measurement units can be implemented as $n_2$ temperature sensors.

To improve ergonomic properties of the device, the temperature sensors can be provided with arrangements for regulated supply of air with a temperature equal to $T_c$, which is obtained by cooling air (e.g. by a method of injecting through a small hole or on the basis of Peltje's elements).

Since the anatomical structure of the bioobject is crucial for locating an organ containing the diagnosed pathology locus, a spatial arrangement map for organs with indication of the topology of the structures of the present bioobject or its part is to be drawn up for each bioobject, and computer programs are to be developed based on said maps, said programs allowing to carry out corresponding diagnosis schemes. To this end, the device is provided with a data processing algorithm index that takes into account a shape of an organ to be diagnosed, and suitable diskettes in an installation set are to be used for installation of a respective algorithm.

To make monitoring of pathology loci easy and automate registration of objects to be diagnosed, the device is provided with a computerized unit that has computer-readable media of databases of bioobjects to be studied, their pathology histories, programs used to compare databases of reference and current values for pictures of various nosologies, programs used to draw isotherms from difference values of temperature value matrices in diagnosing, to determine poles of said isotherms, to realize calculations of a depth of occurrence of pathology loci according to predetermined algorithms, and also to recognize a pathology nature and output information to the visualization unit, and also to print information to a selected storage medium using modems tuned to a selected data transmission channel.

BRIEF DESCRIPTION OF THE DRAWING

The description of the drawing will further be explained by example of diagnostics realization, which example is not unique and assumes presence of other realizations encompassed in combination by features of the claims below.

Figure 1:
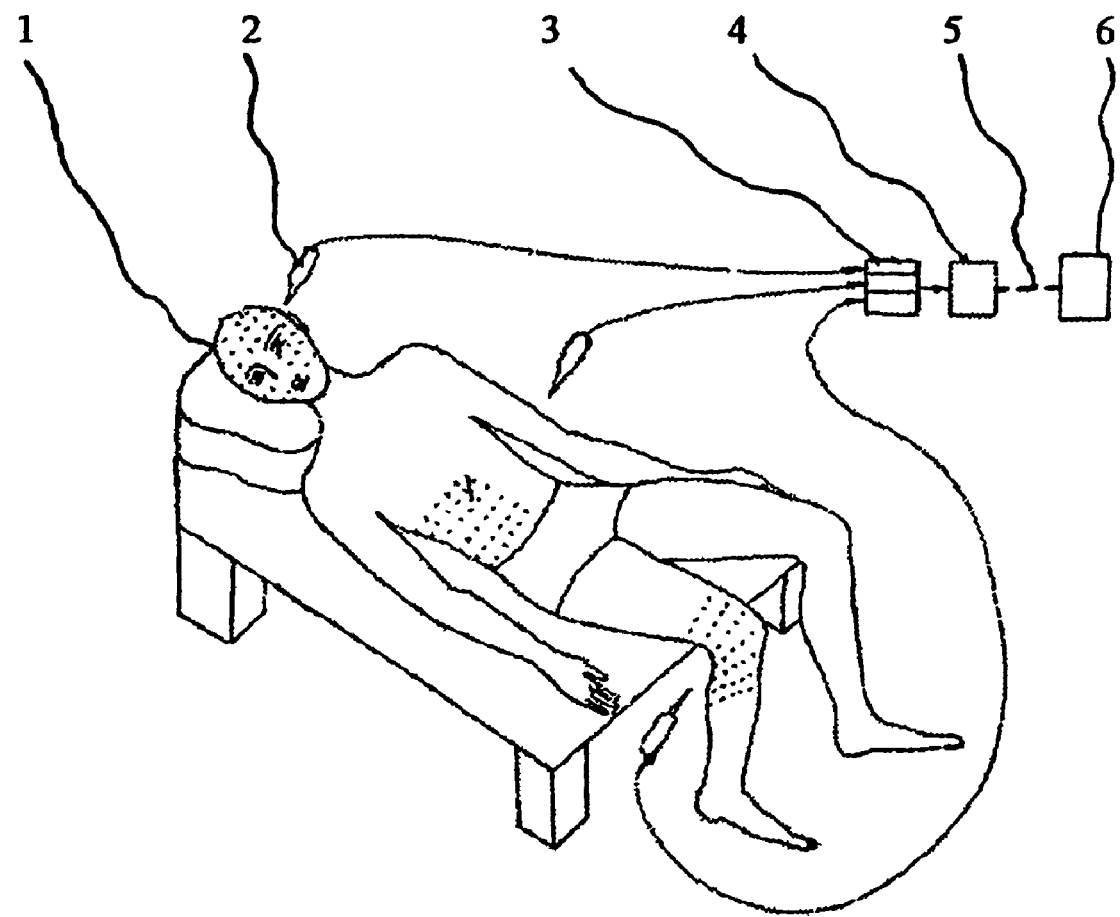
FIG. 1 schematically shows a bioobject who is a person 1. Temperature sensors 2, $n_2$ in number, are connected $n_3$ temperature measurement units 3 connected to RAM units 4 coupled to communication channels 5 and connected to additional temperature measurement, RAM, program realization and visualization units united in an autonomous case 6.

The device operates in as follows. Regularly located points are marked using applied masks or in another way on the skin of the bioobject disposed in a position convenient for operators, said points being deprived of fat with a 40% ethyl alcohol solution. Then, temperature sensors chosen for diagnosing are set in corresponding body areas, and a temperature drop value as compared to a selected base temperature is synchronously measured in each point with each sensor in series. Depending on whether this examination is primary or secondary for the selected body parts, the results are compared with a temperature data array obtained earlier using additional comparator units. Measurement results in all selected temperature measurement channels are supplied to RAM units where they are either stored or sent by communication channels to processing program realization units with subsequent visualization as an image and text documentation based on the diagnosis results.

EMBODIMENT OF DISCLOSED METHOD

Chosen as a diagnosis objects are woman's mammary glands. To examine them, a patient is laid supine on the bed. The mammary glands are wiped with a 40% ethyl alcohol solution and then a pause is given at the base room air temperature of 21° C. that is necessary to render the skin temperature stationary. Then a brassiere is put on the mammary glands to fix them in a vertical position. Holes in the brassiere form points on the surface of the mammary glands as circles each of them contains 8 holes. A number of circles are from 3 to 6 depending upon a height of a mammary gland, and a brassiere size is selected correspondingly. Data of the patient and her size of the brassier are registered into the data of the RAM unit. Then a cycle of examination with a temperature sensor is carried out for each mammary gland, which consists in consecutive measurement of a temperature relative to the base temperature in each point according to a set rule (for instance, clockwise). The measurement cycle in each point consists in the following sequence of operations: selecting a number of a hole, applying a sensor to the skin in the selected hole, getting a sound signal of measurement termination, applying the sensor to a device which fixes the base temperature $T_c$ and getting a sound signal of cooling the sensor down to the base temperature. Then the cycle is repeated for the next point. After termination of measurements, depending upon whether the examination was primary or secondary, either a pattern of pathology distribution and quality in the mammary glands is visualized using an algorithm for processing the resulting temperature data, which was previously put into the computerized unit, or changes occurred after the primary examination are determined. If there is no computer at the location of the patient, a modem is used to transmit data to a computer, said modem receiving information from the device by radio telephone communication.

The offered method and the device by the use of dynamic temperature measurement in a number of regular points on the bloobject surface can find loci and recognize their nature and the location in the bioobject or in the body part. With the purpose of a choice of the best mode of treatment of the bloobject the offered method allows to correct prescribed medical and biological procedures by way of loci monitoring.

INDUSTRIAL APPLICABILITY

The invention can be used in biology and medicine for screening of bioobjects, in particular, for mass screening of population, screening aimed at the formation of female risk groups for mammary checkups, for diagnosing and monitoring various types of neoplasms in bodies of bioobjects, particularly in a human body.

What is claimed is:

1. A method for temperature diagnostics of bioobject pathologies, comprising:
   a) marking a bioobject surface or a body part with a plurality of regular points;
   b) measuring a series of temperatures by means of at least one body temperature sensor at said regular points with respect to time;
   c) obtaining a plurality of asymptotic temperature values at said plurality of regular points by plotting said series of temperature measurements on a curve with respect to time and obtaining from said curve an array of asymptotic temperature values;
   d) storing said array of asymptotic temperature values and obtaining a plurality of isotherm poles therefrom;
   e) from a magnitude value and sign for each of the plurality of isotherm poles, obtaining an averaged temperature value for the bioobject surface, Top, for a pathology locus of depth Z, for a nosology of said pathology locus;
   f) coordinating the array of asymptotic temperature values with a plurality of zones inside the bioobject body, the zones being identified with pathology loci responsible for the temperatures measured in (a) and (b), to getting coordinates of said pathology loci.

2. The method of claim 1, further comprising:
   g) iteratively repeating step (b) and obtaining a secondary array of surface temperature values with respect to time;
   h) obtaining an array of surface temperature difference values by subtracting the primary array from the secondary array and thereby obtaining a plurality of asymptotic temperature difference values at the plurality of regular points;
   i) storing said array of asymptotic temperature difference values and obtaining a plurality of isotherm poles therefrom:
   i) coordinating the array of asymptotic temperature difference values with a plurality of zones inside the bioobject body, each zones being identified with a pathology locus, with changes monitored in the pathology loci.

3. A method of claim 1 wherein, in case of a positive deviation values of the magnitude value and a positive sign of the temperature change took place in the isotherm pole as specified in step d) the depth of the pathology locus (Z) is determined by the criterion:

$$Z \propto r \sqrt{\frac{2T^2}{T_0^2 - T^2} - 1},$$

where r is the current radius counted from the isotherm pole, $T_0$ is the temperature value at the isotherm pole, T is the current temperature value in polar coordinates with the center of the isotherm pole.

4. A method of claim 1 wherein, in case of a negative deviation values of the magnitude value and a negative sign of the temperature change took place in the isotherm pole as specified in step d) the depth of the pathology locus (Z) is determined by the criterion:

$$Z \propto \sqrt{\frac{r^2}{\left(\frac{T_0}{T}\right)^{\frac{2}{3}}} - 1},$$

where r is the current radius counted from the isotherm pole. $T_0$ is the temperature value at the isotherm pole, T is the current temperature value in polar coordinates with the center of the isotherm pole.

5. A method of claim 1, wherein, in case of the most dangerous pathology locus where temperature is higher than an average temperature $T_{cp}$, an averag temperature value $T_{loc}$ in the pathology locus can be estimated by th criterion:

$$T_{loc} \propto \frac{\Theta}{4\pi\rho} + T_{cp},$$

where $\Theta$ is a thermal current flowing through the bioobject surface and caused by the pathology locus with the higher temperature and $\rho$ is a typical pathology locus size.

6. The method of claim 5, wherein a respective nosology type is assigned to a pathology locus according to a magnitude end sign of a temperature change in a locus depending upon an average temperature $T_{loc}$ and its location in a respective organ of the body.

7. The method of claim 6, wherein nosology types for pathological loci are represented as average statistical pictures which can be used as spatial filters for the subsequent comparison of diagnosing results.

8. The method of claim 7, wherein, for monitoring pathology loci, medical and biological procedures are prescribed which act to detected pathology loci, the bioobject or the body part is diagnosed in predetermined time intervals, and results of such diagnostics are used to estimate the action of the prescribed procedures to pathology lad to correct, change or keep said procedures.

* * * * *